United States Patent [19]

Griggs

[11] Patent Number: 4,533,774

[45] Date of Patent: Aug. 6, 1985

[54] PROCESS FOR THE PRODUCTION OF ETHYLENE GLYCOL

[75] Inventor: Colin G. Griggs, Ashford, England

[73] Assignee: The British Petroleum Company p.l.c., London, England

[21] Appl. No.: 554,846

[22] Filed: Nov. 23, 1983

[30] Foreign Application Priority Data

Nov. 27, 1982 [GB] United Kingdom ............... 8233896

[51] Int. Cl.$^3$ .................... C07C 31/20; C07C 29/00
[52] U.S. Cl. ................................ 568/866; 568/852
[58] Field of Search ............................... 568/866, 852

[56] References Cited

U.S. PATENT DOCUMENTS

| | | | |
|---|---|---|---|
| 2,368,494 | 1/1945 | Rosen et al. | 568/866 |
| 2,426,017 | 8/1947 | Hamblet et al. | 568/866 |
| 3,081,357 | 3/1963 | Alderson et al. | 568/852 |
| 3,414,588 | 12/1968 | Jones | 568/852 |
| 3,438,997 | 4/1969 | Fetterly et al. | 568/852 |
| 4,144,401 | 3/1979 | Wall | 568/852 |
| 4,200,765 | 4/1980 | Goetz | 568/852 |
| 4,337,371 | 6/1982 | Kollar | 568/852 |
| 4,356,332 | 10/1982 | Knifton | 568/852 |
| 4,393,252 | 7/1983 | Kollar | 568/852 |
| 4,412,084 | 10/1983 | Kollar | 568/852 |
| 4,412,085 | 10/1983 | Kollar | 568/852 |

FOREIGN PATENT DOCUMENTS 625909  7/1949  United Kingdom ................ 568/852

*Primary Examiner*—J. E. Evans
*Attorney, Agent, or Firm*—Brooks, Haidt, Haffner & Delahunty

[57] ABSTRACT

Ethylene glycol is produced by reacting at elevated temperature methanol, a polymeric source of formaldehyde and an organic peroxide having the formula R—O—O—R$^1$ wherein R and R$^1$ are independently either alkyl or aralkyl groups containing from 3 to 12 carbon atoms. The polymeric source of formaldehyde is preferably paraformaldehyde.

9 Claims, No Drawings

PROCESS FOR THE PRODUCTION OF ETHYLENE GLYCOL

The present invention relates to a process for the production of ethylene glycol.

Ethylene glycol is a very large tonnage industrial chemical which finds direct use in automotive coolant and antifreeze solutions, as a heat-transfer agent in refrigeration, and as an ingredient of deicing fluids for airport runways. Its uses as a chemical intermediate include its incorporation as an essential constituent in polyester fibres, films and bottle resins. It is also used as a solvent in for example lacquers, printing inks and adhesives.

In recent years, emphasis has shifted away from traditional methods of manufacturing ethylene glycol towards routes which utilise synthesis gas (gaseous mixtures comprising carbon monoxide and hydrogen), largely because synthesis gas can be derived not only from petroleum but also from such raw materials as natural gas and coal, and potentially from oil shale and tar sands. Thus, according to U.S. Pat. Nos. 2,316,564; 2,153,064; 2,152,852; 2,285,448; and 2,331,094, ethylene glycol can be produced by reacting formaldehyde with carbon monoxide and water at high pressures (over 300 bars) in the presence of an acid catalyst to produce hydroxyacetic (glycollic) acid, reacting the acid so-produced with methanol to form the methyl ester and thereafter converting the methyl ester to ethylene glycol by catalytic hydrogenation. Another process, disclosed in U.S. Pat. Nos. 4,115,428 and 4,115,433, describes the production of ethylene glycol by reacting methanol and carbon monoxide at high pressures using a rhodium catalyst.

Even more recently, GB patent applications publication Nos. 2083037 and 2083038, U.S. Pat. No. 4,393,252 and European patent publication Nos. 71457 and 71458 relating to the production of ethylene glycol by reacting methanol, formaldehyde and an organic peroxide have appeared. GB-A-2083038 discloses a process for producing ethylene glycol by reacting methanol, an organic peroxide, and formaldehyde in the presence of water (suitably from about 0.5 to about 35 weight percent), said organic peroxide having the formula $R-O-O-R^1$ wherein R and $R^1$ each is an alkyl or aralkyl group containing 3 to 12 carbon atoms, wherein no more than about 6 percent of organic peroxide, based on the total weight of methanol, organic peroxide, formaldehyde and water present, is utilised in the initial reaction mixture. GB-A-2083037 describes a similar process in which a basic material is added to the reactants in an amount sufficient to reduce the hydrogen ions that are being formed in the reaction without unduly reducing the ethylene glycol production due to by-product formation. In Examples 13 and 14 of GB-A-2083037 the monomeric aqueous formaldehyde was produced from paraformaldehyde by adding a small amount of hydrogen chloride to depolymerise the paraformaldehyde to aqueous monomeric formaldehyde and thereafter the formaldehyde solution was neutralised by the addition of a small amount of sodium bicarbonate. U.S. Pat. No. 4,393,252 discloses subject matter similar to that of GB-A-2083037. EP-A-71457 discloses the improvement wherein the formaldehyde and the organic peroxide are added portionwise at intervals throughout the reaction period. Finally EP-A-71458 discloses the improvement wherein the amount of the peroxide used is greater than 6 and up to 25 weight percent and the amounts of water used is from 0.5 to 36 weight percent, and the amount of the peroxide and water used are dependent on each other so that either the amount of the peroxide used is greater than 6 up to 12 weight percent and the amount of water used is from 0.5 to 35 weight percent, or the amount of the peroxide used is greater than 12 up to 15 weight percent and the amount of water used is from 0.5 to 25 weight percent, or the amount of the peroxide used is greater than 15 up to 20 percent and the amount of water used is from 0.5 to 15 weight percent, or the amount of the peroxide used is greater than 20 to 25 weight percent and the amount of water used is from 0.5 to 10 weight percent, the above weight percentages being based on the total weight of the methanol, organic peroxide, formaldehyde and water present in the reaction mixture.

We have now found that a polymeric source of formaldehyde can be employed without adding acid to depolymerise it to monomeric formaldehyde, thereby eliminating the acid neutralisation step. Moreover, using substantially anhydrous conditions and a polymeric source of formaldehyde better conversions to ethylene glycol can be achieved and in particular increased ratios of ethylene glycol to dialkyl peroxide can be obtained at low peroxide initiator levels.

Accordingly, the present invention provides a process for the production of ethylene glycol which process comprises reacting at elevated temperature methanol, a polymeric source of formaldehyde and an organic peroxide having the formula $R-O-O-R^1$ wherein R and $R^1$ are independently either alkyl or aralkyl groups containing from 3 to 12 carbon atoms.

Suitable polymeric sources of formaldehyde include paraformaldehyde, otherwise known as paraform, trioxane and tetraoxane, of which paraformaldehyde is preferred. Paraformaldehyde is a solid mixture of linear poly(oxymethylene glycols) of relatively short chain length and may be represented by the formula $HO(CH_2O)_nH$, wherein n is 8–100. Commercially available forms of paraformaldehyde generally have an average molecular weight of about 600 and may contain up to about 9 wt % water and a maximum acidity as formic acid of 0.03 wt %. Such commercially available forms may be used in the process of the present invention without further purification. Alternatively, the commercially available forms may be further purified before use in the process. If desired, higher molecular weight, i.e. n greater than 100, suitably in the range from 100 to 500, forms of polyoxymethylene glycols of the formula $HO(CH_2O)_nH$ may be employed. Trioxane, which may also be used in the process of the present invention is the cyclic symmetrical trimer of formaldehyde and is also a solid. Trioxane is also commercially available. Tetraoxane, which is a cyclic tetramer of formaldehyde, is a solid.

The organic peroxide having the formula $R-O-O-R^1$ wherein R and $R^1$ are independently either alkyl or aralkyl groups containing from 3 to 12 carbon atoms may suitably be di-tertiary-butyl peroxide, di-cumyl peroxide, tertiary-butyl cumyl peroxide or tertiary-butyl ethyl benzyl peroxide. Preferably the peroxide is either di-cumyl peroxide or ditertiary-butyl peroxide.

The process may be operated in the presence of water, using reactants which have not been dried, optionally with additional water. Thus a typical feed may comprise from about 45 to about 97% by weight, preferably from about 80 to about 90% by weight of methanol, from about 0.5 to about 50% by weight, preferably from about 2 to about 12% by weight of the polymeric source of formaldehyde, from about 0.25 to about 15% by weight, preferably from about 0.75 to about 3% by weight of organic peroxide and from about 0.5 to about 35% by weight of water, all percentages by weight being based on the total weight of the reactants.

However, as mentioned hereinabove, it is preferred to operate the process of the invention under substantially anhydrous conditions, ie at a water content of less than 0.5% by weight, preferably less than 0.25% by weight, based on the total weight of the reactants. It may be necessary when operating under substantially anhydrous conditions to use at least partially dried reactants.

As regards the reaction conditions, the process may suitably be operated at a temperature greater than 100° C., for example in the range 100° to 200° C., preferably from 125° to 175° C. Under certain conditions, it may be desirable to operate at a temperature below 100° C. The process may be operated at autogenous pressure, that is the pressure generated in a closed reactor at the particular reaction temperature though pressures above and below autogenous may be used if so desired. Generally, the reaction time for a batch operation may suitably be in the range from 0.25 to 8 hours, preferably from 0.5 to 4 hours.

The process may be operated batchwise, semi-continuously or continuously, preferably continuously. Suitable methods of operation are described in the aforesaid EP-A-71457 and EP-A-71458, for example. Such methods include the portionwise addition of the organic peroxide and polymeric source of formaldehyde at intervals throughout the reaction period. The product mixture may be purified using conventional techniques, such as distillation or solvent extraction, to recover ethylene glycol of the desired purity. Besides ethylene glycol, there may also be formed by-products, such as t-butanol, methylal, methyl formate, glycerine and acetone. Since methylal is not an ethylene glycol precursor, its formation may lower the productivity of the process on a once-through basis. For this reason it is preferred to attempt to suppress methylal by-product formation by addition to the reactants of a basic material in an amount sufficient to reduce the hydrogen ions that are being formed in the reaction without unduly reducing ethylene glycol production. Suitable basic materials are defined and exemplified in GB-A-2083037, to which the reader is hereby referred.

The invention will now be illustrated by reference to the following Examples. The paraformaldehyde, as used in the Examples, was supplied by Fisons. It conforms with the formula $HO(CH_2O)_nH$ wherein n is in the range from 8 to 100 and has an average value of about 60. The water content of the paraformaldehyde is less than or equal to 2%, the formaldehyde content is about 97% and the rest is methanol.

EXAMPLES 1 TO 6

Into a 100 ml autoclave was weighed paraformaldehyde, di-tertiary-butyl peroxide (DTBP) and methanol and the autoclave closed and sealed. The autoclave and contents were then heated to 155° C. and held at this temperature for 2 hours. At the end of the reaction period the autoclave was cooled, opened and its contents analysed by gas chromatography. The compositions of the initial reaction mixtures and the analyses of the reaction products are given in the accompanying Table.

The ratio of glycol (EG) to peroxide (DTBP) increased with decreasing peroxide level. Particularly noteworthy are Examples 1 and 2 which show higher ratios of EG/DTBP than those reported in GB No. 2083038A using aqueous formaldehyde.

EXAMPLES 7-9

The procedure of Examples 1 to 6 was repeated except that water was added to the initial reactants. The compositions of the initial reaction mixture and the analyses of the reaction products are given in Table 2.

EXAMPLES 10-17

The procedure of Examples 1 to 6 was repeated except that di-cumyl peroxide (DCP) was used in place of di-t-butylperoxide and that Examples 10, 12, 14 and 16 had reaction times of only one hour. The compositions etc are shown in Table 3. Noteworthy are the high EG/DCP ratios obtained at low peroxide level. The Examples also illustrate the effect of reaction time, the reactions with DCP being faster than those with DTBP and largely complete after one hour.

EXAMPLES 18-21

The procedure of Examples 1 to 6 was repeated except that the autoclave and contents were heated to different temperatures. The compositions of the initial reaction mixtures and the analyses of the reaction products are given in Table 4.

EXAMPLES 22-28

The procedure of examples 1 to 6 was repeated. The compositions of the initial reaction mixtures and the analyses of the reaction products are given in Table 5. The Examples illustrate the variations in ethylene glycol yield and its ratio to DTBP which are obtained on varying methanol and paraformaldehyde concentrations whilst keeping the initial peroxide level constant.

TABLE 1

EFFECT OF VARYING THE INITIAL [DTBP] WITH RESPECT TO THE EG YIELD

| Example | initial wt % | | | mmol EG/mmol DTBP | final wt % | | TBA SELECT * | Temp (°C.) | Time (hr) |
| --- | --- | --- | --- | --- | --- | --- | --- | --- | --- |
| | DTBP | $(CH_2O)_n$ | $CH_3OH$ | | EG | DMM | | | |
| 1 | 0.44 | 11.1 | 88.5 | 24.39 | 4.6 | 3.1 | 58 | 155 | 2 |
| 2 | 0.76 | 9.5 | 89.8 | 14.6 | 4.6 | 3.4 | 49 | 155 | 2 |
| 3 | 1.1 | 9.1 | 89.8 | 8.8 | 4.2 | 2.5 | 55 | 155 | 2 |
| 4 | 2.2 | 9.0 | 88.8 | 5.7 | 5.4 | 2.8 | 49 | 155 | 2 |
| 5 | 5.9 | 15.8 | 78.2 | 2.6 | 6.5 | 4.6 | 45 | 155 | 2 |

TABLE 1-continued

EFFECT OF VARYING THE INITIAL [DTBP] WITH RESPECT TO THE EG YIELD

| Example | initial wt % DTBP | initial wt % $(CH_2O)_n$ | initial wt % $CH_3OH$ | mmol EG/mmol DTBP | final wt % EG | final wt % DMM | TBA SELECT * | Temp (°C.) | Time (hr) |
|---|---|---|---|---|---|---|---|---|---|
| 6 | 10.3 | 8.2 | 81.5 | 2.6 | 11.5 | 1.8 | 50 | 155 | 2 |

DTBP = di-t-butyl peroxide, EG = ethylene glycol, DMM = dimethoxymethane, TBA = t-butyl alcohol.

*TBA SELECT = t-butylalcohol selectivity = $\frac{\text{mmol of TBA obtained}}{2 \times (\text{mmol of TBBP}) \text{ added}}$ $(CH_2O)_n$ = paraformaldehyde

TABLE 2

EFFECT OF ADDING WATER TO THE INITIAL REACTANTS WITH RESPECT TO EG YIELD

| Example | initial wt % DTBP | initial wt % $(CH_2O)_n$ | initial wt % $CH_3OH$ | initial wt % $H_2O$ | mmol EG/ mmol DTBP | final wt % EG | Temp (°C.) | Time (hr) |
|---|---|---|---|---|---|---|---|---|
| 7 | 1.7 | 6.6 | 82.1 | 9.6 | 2.43 | 1.72 | 155 | 2 |
| 8 | 2.0 | 7.0 | 80.9 | 10.1 | 3.0 | 2.52 | 155 | 2 |
| 9 | 2.3 | 9.0 | /5.7 | 13.0 | 5.31 | 5.32 | 155 | 2 |

TABLE 3

EFFECT OF REACTION TIME AND [DCP] ON EG YIELD

| Example | initial wt % DTBP | initial wt % $(CH_2O)_n$ | initial wt % $CH_3OH$ | mmol EG/ mmol DTBP | final wt % EG | final wt % DMM | Temp (°C.) | Time (hr) |
|---|---|---|---|---|---|---|---|---|
| 10 | 0.56 | 9.5 | 89.9 | 16.0 | 2.1 | 1.1 | 155 | 1 |
| 11 | 0.56 | 9.5 | 89.9 | 18.9 | 2.5 | 2.2 | 155 | 2 |
| 12 | 1.1 | 9.1 | 89.8 | 13.3 | 3.5 | 1.6 | 155 | 1 |
| 13 | 1.1 | 9.1 | 89.8 | 14.8 | 3.8 | 2.1 | 155 | 2 |
| 14 | 2.2 | 9.0 | 88.8 | 6.3 | 3.3 | 1.5 | 155 | 1 |
| 15 | 2.2 | 9.0 | 88.8 | 6.6 | 3.4 | 2.4 | 155 | 2 |
| 16 | 4.4 | 8.8 | 86.8 | 5.6 | 5.8 | 1.6 | 155 | 1 |
| 17 | 4.4 | 8.8 | 86.8 | 5.8 | 5.6 | 2.2 | 155 | 2 |

TABLE 4

EFFECT OF TEMPERATURE ON EG YIELD FOR A STANDARD SET OF CONDITIONS

| Example | initial wt % DTBP | initial wt % $(CH_2O)_n$ | initial wt % $CH_3OH$ | mmol EG/ mmol DTBP | final wt % EG | final wt % DMM | Temp (°C.) | Time (hr) |
|---|---|---|---|---|---|---|---|---|
| 18 | 2.2 | 9.0 | 88.8 | 0.9 | 0.9 | — | 100 | 2 |
| 19 | 2.2 | 9.0 | 88.8 | 2.7 | 2.6 | 0.5 | 125 | 2 |
| 20 | 2.2 | 9.0 | 88.8 | 8.8 | 5.4 | 2.8 | 155 | 2 |
| 21 | 2.2 | 9.0 | 88.8 | 3.6 | 3.4 | 4.1 | 175 | 2 |

TABLE 5

EFFECT ON EG YIELD, HOLDING [DTBP] CONSTANT, WHILST VARYING THE [$CH_3OH$] AND [$(CH_2O)_n$]

| Example | initial wt % DTBP | initial wt % $(CH_2O)_n$ | initial wt % $CH_3OH$ | mmol EG/ mmol DTBP | final wt % EG | final wt % DMM | Temp (°C.) | Time (hr) |
|---|---|---|---|---|---|---|---|---|
| 22 | 2.2 | 2.2 | 95.6 | 3.5 | 3.2 | 0.8 | 155 | 2 |
| 23 | 2.2 | 4.5 | 93.3 | 6.1 | 5.8 | 1.4 | 155 | 2 |
| 24 | 2.2 | 9.0 | 88.8 | 5.7 | 5.4 | 2.8 | 155 | 2 |
| 25 | 2.2 | 18.0 | 79.8 | 4.5 | 4.3 | 5.1 | 155 | 2 |
| 26 | 2.2 | 26.9 | 70.9 | 2.8 | 2.7 | 4.0 | 155 | 2 |
| 27 | 2.2 | 35.8 | 62.0 | 2.6 | 2.4 | 4.3 | 155 | 2 |
| 28 | 2.2 | 44.7 | 53.0 | 2.2 | 2.1 | 2.6 | 155 | 2 |

I claim:

1. In a process for the production of ethylene glycol by reacting at elevated temperature methanol, formaldehyde, and an organic peroxide having the formula R—O—O—R¹ wherein R and R¹ are independently either alkyl or aralkyl groups containing from 3 to 12 carbon atoms,
   the improvement which comprises adding the formaldehyde in the form of a polymeric source thereof, and
   wherein the amount of water present is less than 0.5% by weight, based on the total weight of reactants.

2. A process according to claim 1 wherein the polymeric source of formaldehyde is trioxane.

3. A process according to claim 1 wherein the polymeric source of formaldehyde is paraformaldehyde.

4. A process according to claim 3 wherein the paraformaldehyde is of the formula $HO(CH_2O)_nH$, wherein n is from 8 to 100.

5. A process according to claim 1 wherein the organic peroxide is either di-cumyl peroxide or ditertiary-butyl peroxide.

6. A process according to claim 1 wherein the amount of water present is less than 0.25% by weight based on the total weight of reactants.

7. A process according to claim 1 wherein the elevated temperature is in the range from 125° to 175° C.

8. A process according to claim 1 wherein the amount of methanol is in the range from about 45 to 97% by weight, the amount of the polymeric source of formaldehyde is in the range from about 0.5 to about 50% by weight, and the amount of organic peroxide is in the range from about 0.25 to about 15% by weight, all percentages by weight being based on the total weight of the reactants.

9. A process according to claim 1 wherein the amount of methanol is in the range from 80 to 90% by weight, the amount of the polymeric source of formaldehyde is in the range from about 2 to about 12% by weight, and the amount of organic peroxide is in the range from about 0.75 to about 3% by weight, all percentages by weight being based on the total weight of the reactants.

* * * * *

UNITED STATES PATENT AND TRADEMARK OFFICE
CERTIFICATE OF CORRECTION

PATENT NO. : 4,533,774

DATED : August 6, 1985

INVENTOR(S) : COLIN G. GRIGGS

It is certified that error appears in the above-identified patent and that said Letters Patent is hereby corrected as shown below:

Col. 2, line 11, after "20", the word --weight-- has been omitted.

Col. 2, line 13, after "20" the word --up-- has been omitted.

Cols. 5-6, Table 2, in the line for Example 9, the figures under $CH_3OH$ should read --75.7--

Signed and Sealed this

Fifth Day of November 1985

[SEAL]

Attest:

Attesting Officer

DONALD J. QUIGG

Commissioner of Patents and Trademarks